US00PP33500P2

(12) United States Plant Patent
Korlipara

(10) Patent No.: US PP33,500 P2
(45) Date of Patent: Sep. 21, 2021

(54) ***LEUCANTHEMUM* PLANT NAMED 'MOUNT HOOD'**

(50) Latin Name: ***Leucanthemum* x *superbum***
Varietal Denomination: Mount Hood

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/212,164

(22) Filed: Mar. 25, 2021

(51) Int. Cl.
*A01H 6/14* (2018.01)
*A01H 5/02* (2018.01)

(52) U.S. Cl.
USPC ..... Plt./285

(58) Field of Classification Search
USPC ..... Plt./285
See application file for complete search history.

*Primary Examiner* — Annette H Para
(74) *Attorney, Agent, or Firm* — Klarquist Sparkman, LLP

(57) ABSTRACT

A new and distinct *Leucanthemum* plant provided herein is characterized by double daisy type inflorescences, pale yellow flower buds and young ray florets, fully open inflorescences display numerous white ray florets with cut and notched tips around a moderate, partially filled yellow gold disc, excellent bloom size, excellent compact habit, and excellent vigor.

2 Drawing Sheets

Botanical denomination: *Leucanthemum* x *superbum*.
Variety designation: 'Mount Hood'.

The present invention relates to a new and distinct cultivar of *Leucanthemum* x *superbum* and given the cultivar name 'Mount Hood'. *Leucanthemum* is in the family Asteraceae. This new cultivar originated from a controlled cross between unnamed, proprietary *Leucanthemum* x *superbum* seedlings. The seed of many crosses was massed so the exact parents are unknown.

Compared to *Leucanthemum* 'Bridal Bouquet', U.S. Plant Pat. No. 24,260, the new cultivar is slightly taller and the inflorescences are larger, and more double.

This new *Leucanthemum* cultivar is distinguished as unique with its:

1. very double daisy type inflorescences,
2. pale yellow flower buds and young ray florets,
3. fully open inflorescences display numerous white ray florets with frilly tips around a small yellow-gold disc,
4. excellent bloom size,
5. an excellent, compact habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
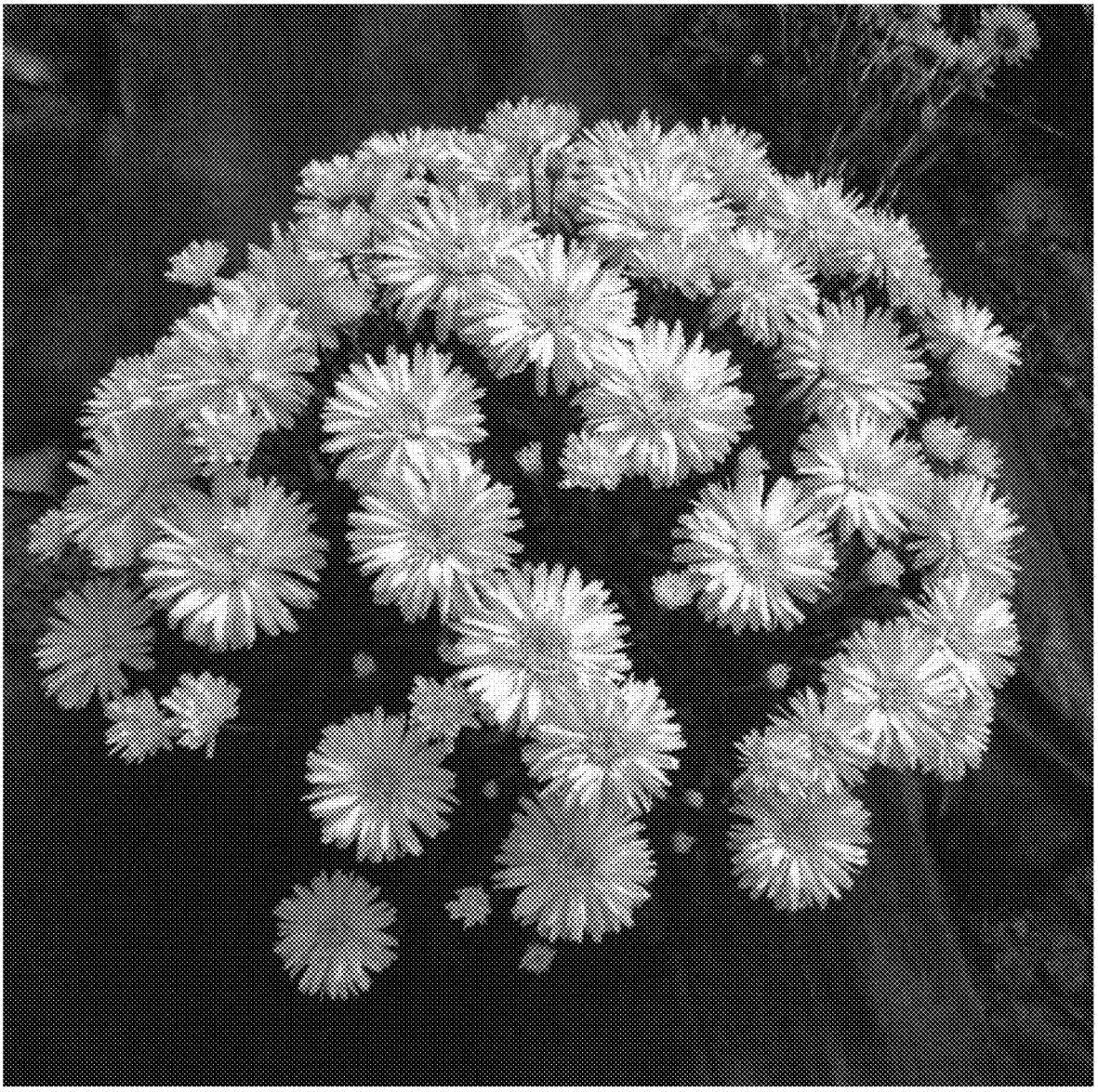
FIG. 1 shows an 18-month-old plant growing in the ground in full sun in the trial field (in mid-July) in Canby, Oreg.
Figure 2:
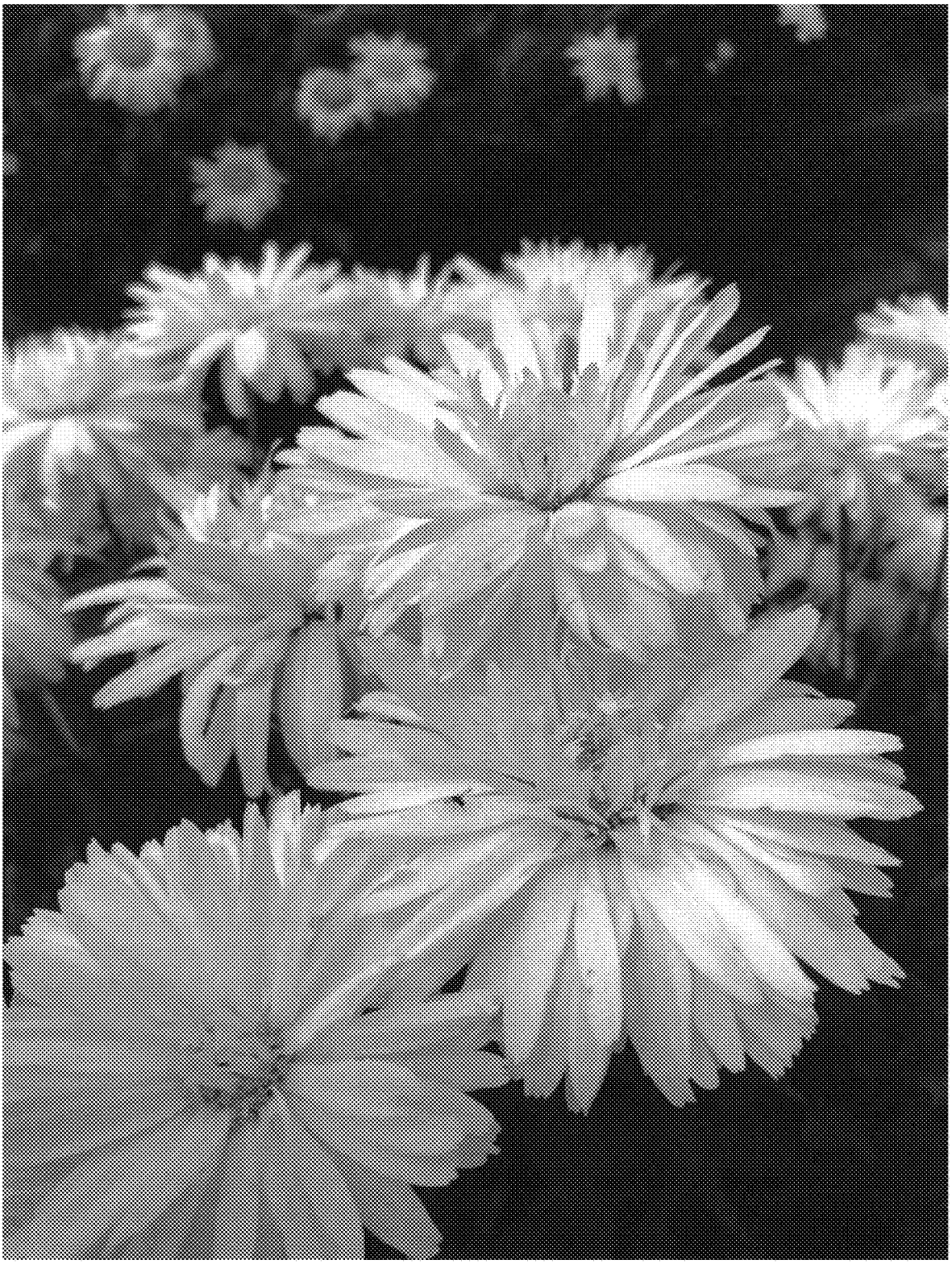
FIG. 2 shows a close-up of the inflorescences.

The following is a detailed description of the new *Leucanthemum* cultivar based on observations of an 18-month-old specimens growing in the field in full sun under typical outdoor conditions in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The *Royal Horticultural Society Colour Chart,* 5$^{th}$ edition, 2007.

Plant:
- *Type*.—Herbaceous perennial.
- *Hardiness*.—USDA Zones 5 to 9.
- *Size*.—39 cm wide and 40 cm tall to top of inflorescences.
- *Form*.—Basal clump.
- *# crowns*.—13.
- *Vigor*.—Excellent.

Stem (flowering):
- *Type*.—Ascending with thick, strong stems.
- *Number of stems*.—About 13 stems from the crown, each flowering with 5 to 14 flowers per stem.
- *Size*.—Grows to about 34 cm tall to a terminal inflorescence and 7 mm wide at base.
- *Internode length*.—2 cm to 4 cm.
- *Surface texture*.—Pubescent.
- *Color*.—Green 137B.

Leaves:
- *Type*.—Simple.
- *Shape*.—Lanceolate.
- *Arrangement*.—Alternate.
- *Blade size*.—Grows to 10 cm long and 30 mm wide.
- *Margins*.—Coarsely serrate.
- *Apex*.—Acute.
- *Base*.—Clasping.
- *Surface texture*.—Pubescent on both sides.
- *Venation*.—Pinnate.

*Petiole*.—Sessile.

*Color*.—Topside Green N137B with main vein Green 137B, bottom side Yellow Green 147B with main vein Yellow Green 147C.

Inflorescence:

*Type*.—Composite on terminal stalked heads.

*Number of inflorescences per plant*.—About 60.

*Size*.—Grows to 10 cm wide and 11 cm deep.

*Form*.—Ray florets held upright when young, lower ray florets reflex down with maturity, mature disc is mostly flat.

*Bud* (*immature inflorescence*).—15 mm wide and 11 mm deep, ray florets held vertically and cupped inwards, White NN155C on top.

*Ray florets*.—With 1 pistil and no stamen, about 90 in number, about 75 normal sized, 15 being smaller near the disc florets, tip 2 to 4 lobed (1 to 3 deeply parted segments), margins entire, base attenuate, average size 3.5 cm long and 5 mm wide, glabrous on both sides; and Yellow Green Group N144C when young maturing to White NN155D on both sides; pistil 4 mm long, ovary 1.5 mm long, Yellow Green 149D, style 2.5 mm long, White NN155B, 2-branched stigma 0.5 mm long, Yellow 13D.

*Disc*.—Slightly concave becoming convex, becoming 10 mm deep and 24 mm wide with maturity, Yellow Orange 15A.

*Disc florets*.—About 200 in number, each 6 mm long and 1.5 mm wide; corolla tubular, 4 mm long and 1.2 mm wide, 5 lobed, glabrous, Yellow 14B on top half and Yellow Green 145B on the bottom half; pistil 1, 5.5 mm long, ovary 2 mm long and Greyed Green 193D, style 2 mm long, Greyed Orange 168C, 2 branched stigma 1 mm long, Greyed Orange 163B; stamen 5 in number, 4 mm long, filaments 2 mm long, Greyed Green 193D, anthers 1.5 mm Greyed Orange N163C, pollen Yellow Orange 21B.

*Involucral bracts*.—About 50 in number, in 3 imbricate whorls, area 2.5 cm wide and 10 mm deep, lobes lanceolate, grow to 7 mm long and 2.5 mm wide, Yellow Green 146B, margin membranous and Brown N200A, tip acute, slightly pubescent on backside and glabrous on inside.

*Receptacle*.—Grows to 16 mm wide and 4 mm deep, Yellow Green 146B.

*Bloom period*.—July through September in Canby, Oreg.

*Fragrance*.—None.

*Lastingness*.—Each inflorescence lasts about three weeks in Canby, Oreg.

Seeds: None seen.

Fertility: Low.

Disease and pests: The new cultivar is typical to the genus. No known resistances to pests or diseases. No problems have been found in Canby, Oreg.

I claim:

1. A new and distinct *Leucanthemum* plant as herein illustrated and described.

* * * * *